(12) United States Patent
Ellman

(10) Patent No.: US 10,327,840 B2
(45) Date of Patent: Jun. 25, 2019

(54) ELECTROSURGICAL HANDPIECE

(71) Applicant: Alan G Ellman, Hewlett, NY (US)

(72) Inventor: Alan G Ellman, Hewlett, NY (US)

(*) Notice: Subject to any disclaimer, the term of this patent is extended or adjusted under 35 U.S.C. 154(b) by 352 days.

(21) Appl. No.: 15/295,860

(22) Filed: Oct. 17, 2016

(65) Prior Publication Data

US 2017/0056100 A1 Mar. 2, 2017

Related U.S. Application Data

(62) Division of application No. 14/207,990, filed on Mar. 13, 2014, now abandoned.

(51) Int. Cl.
*A61B 18/14* (2006.01)
*A61B 17/32* (2006.01)
*A61B 18/00* (2006.01)

(52) U.S. Cl.
CPC .. *A61B 18/1477* (2013.01); *A61B 17/320068* (2013.01); *A61B 18/1402* (2013.01); *A61B 2017/320088* (2013.01); *A61B 2018/00029* (2013.01); *A61B 2018/0072* (2013.01); *A61B 2018/00178* (2013.01); *A61B 2018/00642* (2013.01); *A61B 2018/00702* (2013.01); *A61B 2018/00714* (2013.01); *A61B 2018/00732* (2013.01); *A61B 2018/00755* (2013.01); *A61B 2018/00761* (2013.01); *A61B 2018/00767* (2013.01); *A61B 2018/00779* (2013.01); *A61B 2018/00791* (2013.01); *A61B 2018/00845* (2013.01); *A61B 2018/00886* (2013.01); *A61B 2018/00898* (2013.01); *A61B 2018/00916* (2013.01); *A61B 2018/00928* (2013.01); *A61B 2018/00994* (2013.01); *A61B 2018/144* (2013.01); *A61B 2018/1407* (2013.01); *A61B 2018/1412* (2013.01); *A61B 2018/1495* (2013.01); *A61B 2218/003* (2013.01)

(58) Field of Classification Search
CPC ............ A61B 18/1477; A61B 18/1402; A61B 2018/00178; A61B 2018/00702; A61B 2018/00779; A61B 2018/00916; A61B 2018/00928; A61B 2018/00642; A61B 2018/00898; A61B 2018/144; A61B 2018/1495
USPC ............................................... 606/41, 42, 46
See application file for complete search history.

(56) References Cited

U.S. PATENT DOCUMENTS

| | | | |
|---|---|---|---|
| 2008/0009853 A1 | 1/2008 | Martin | |
| 2012/0330307 A1* | 12/2012 | Ladtkow | A61B 18/1482 606/42 |
| 2013/0006239 A1 | 1/2013 | Pikramenos | |
| 2013/0046299 A1 | 2/2013 | Newkirk | |

OTHER PUBLICATIONS

International Search Report and written opinion for PCT/US 2014/026898 filed Mar. 13, 2014.

* cited by examiner

*Primary Examiner* — Thomas A Giuliani

(57) ABSTRACT

An electrosurgical tool includes an electrically powered handpiece with a detachable electrode at one end and a power connection at the other. A mechanism for connecting the detachable electrode to the handpiece includes a keyed electrical connection to power the electrode. The handpiece includes a feedback controller incorporated in the tool to adjust operational characteristics of the electrosurgical tool.

5 Claims, 10 Drawing Sheets

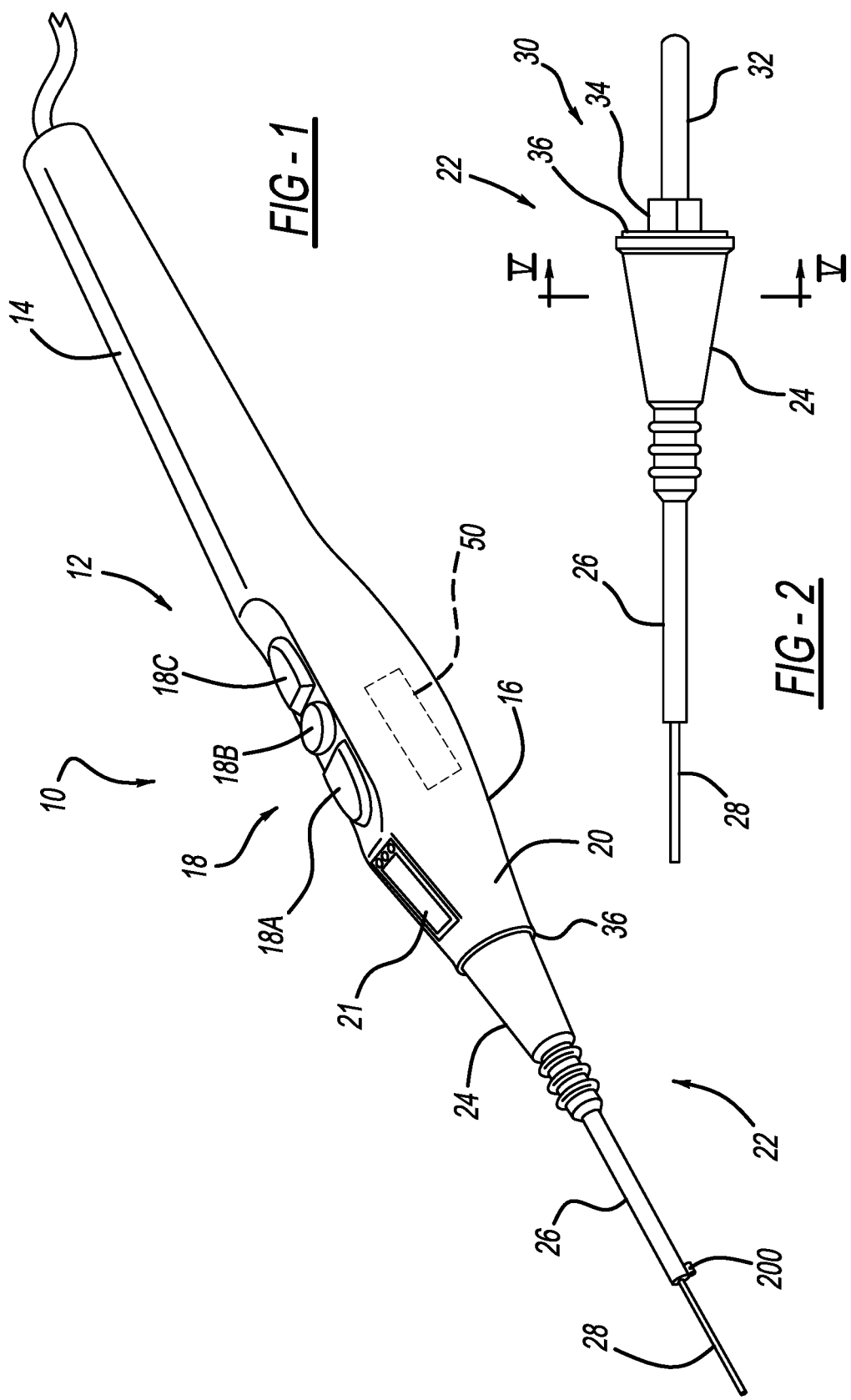

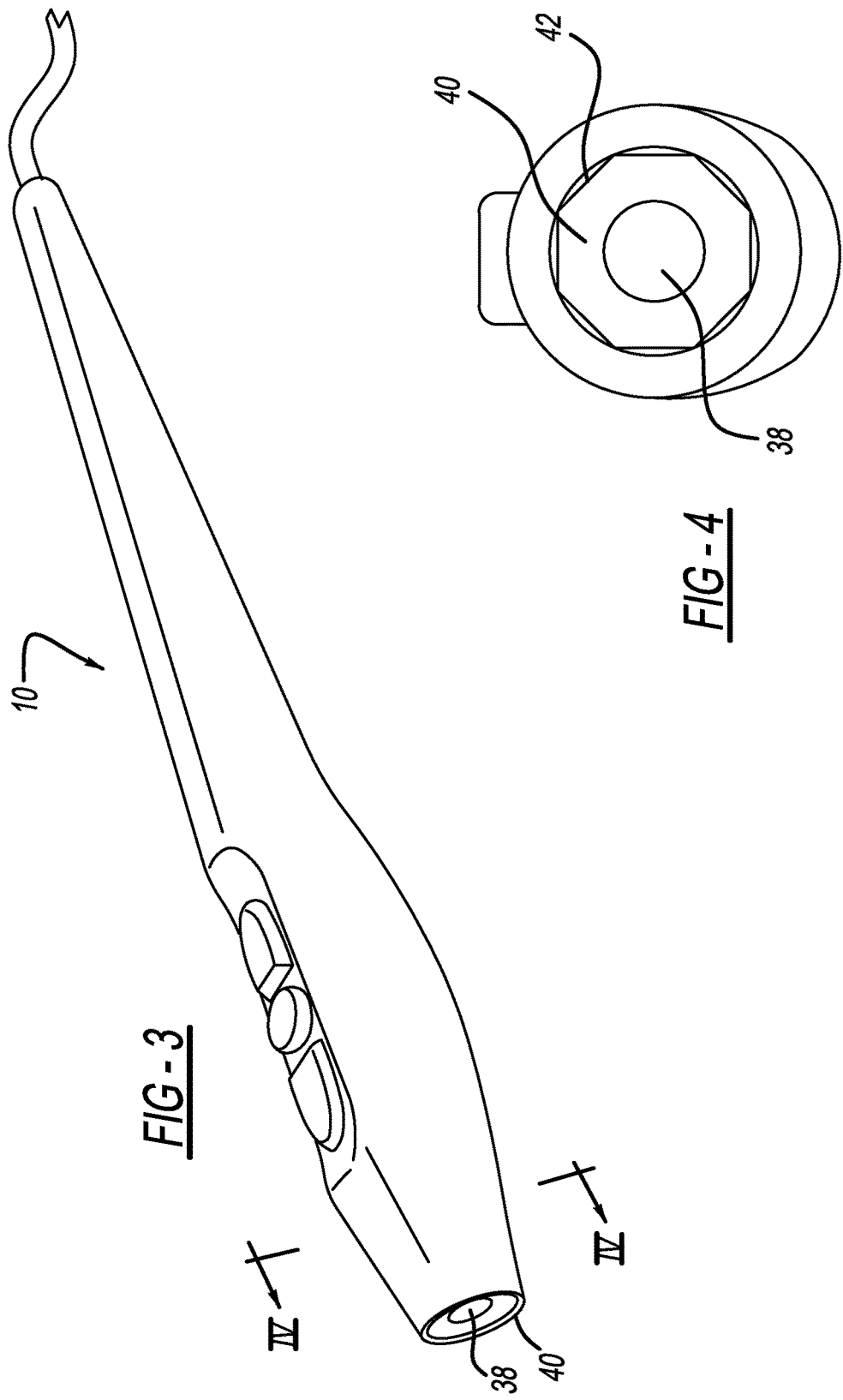

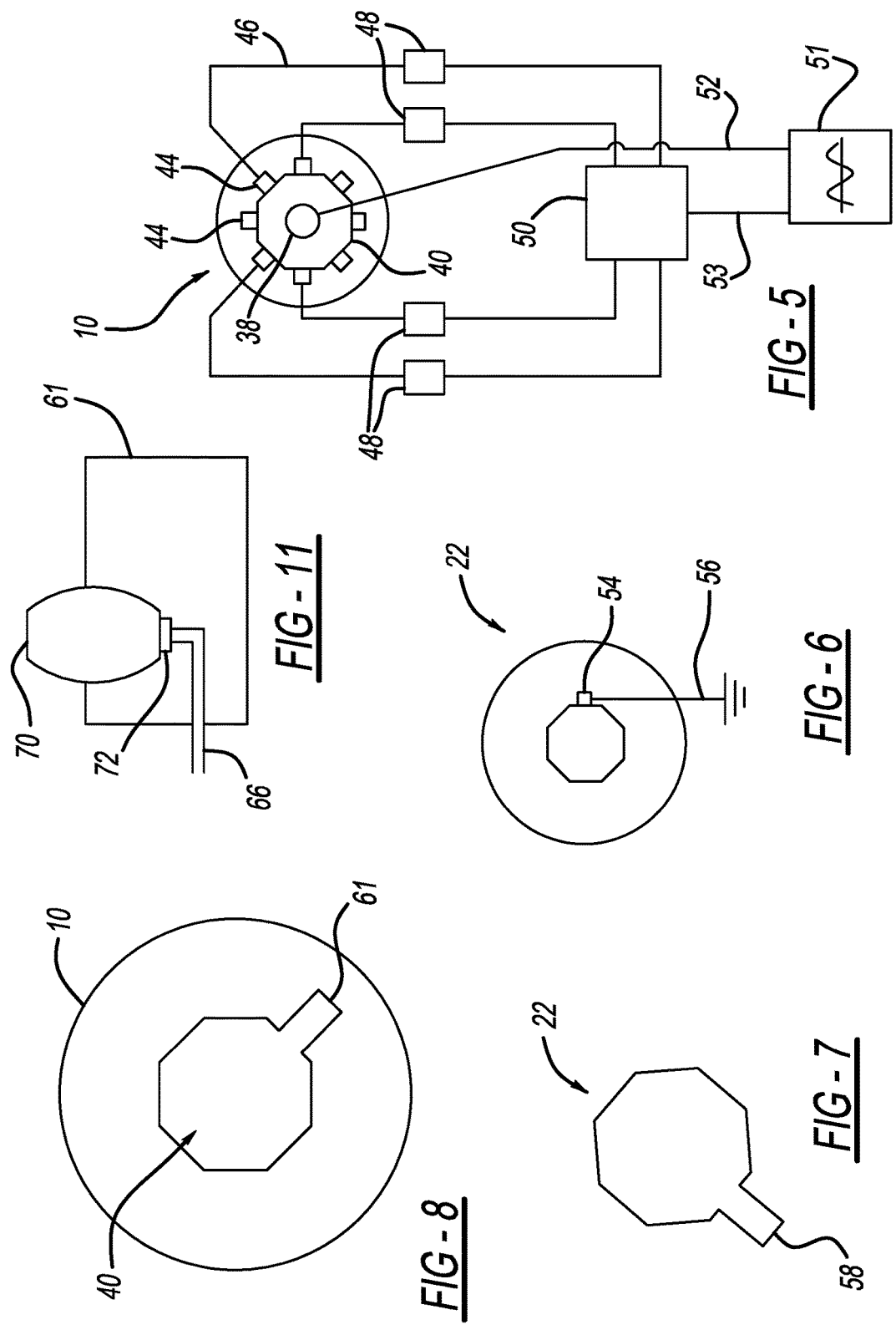

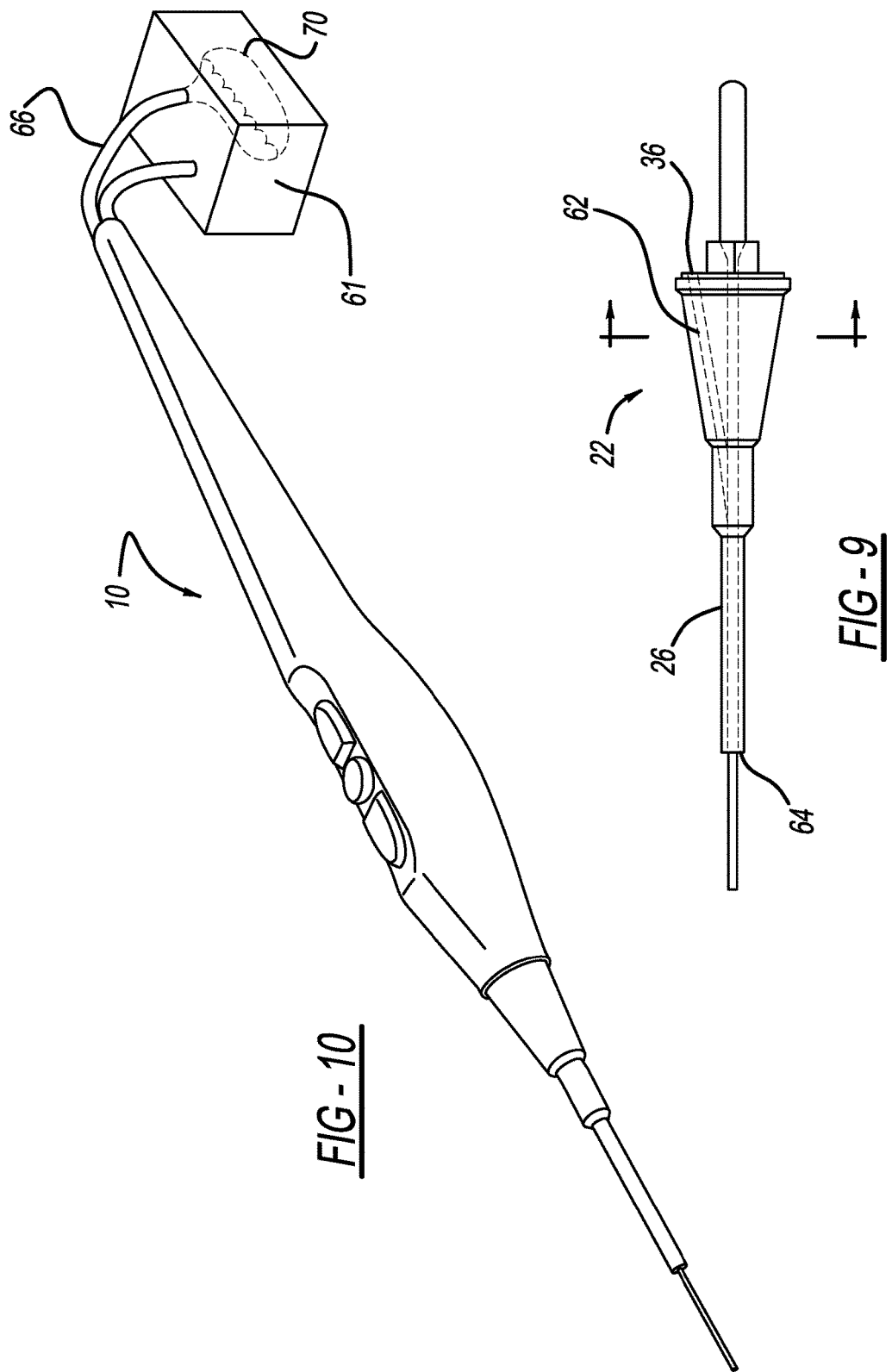

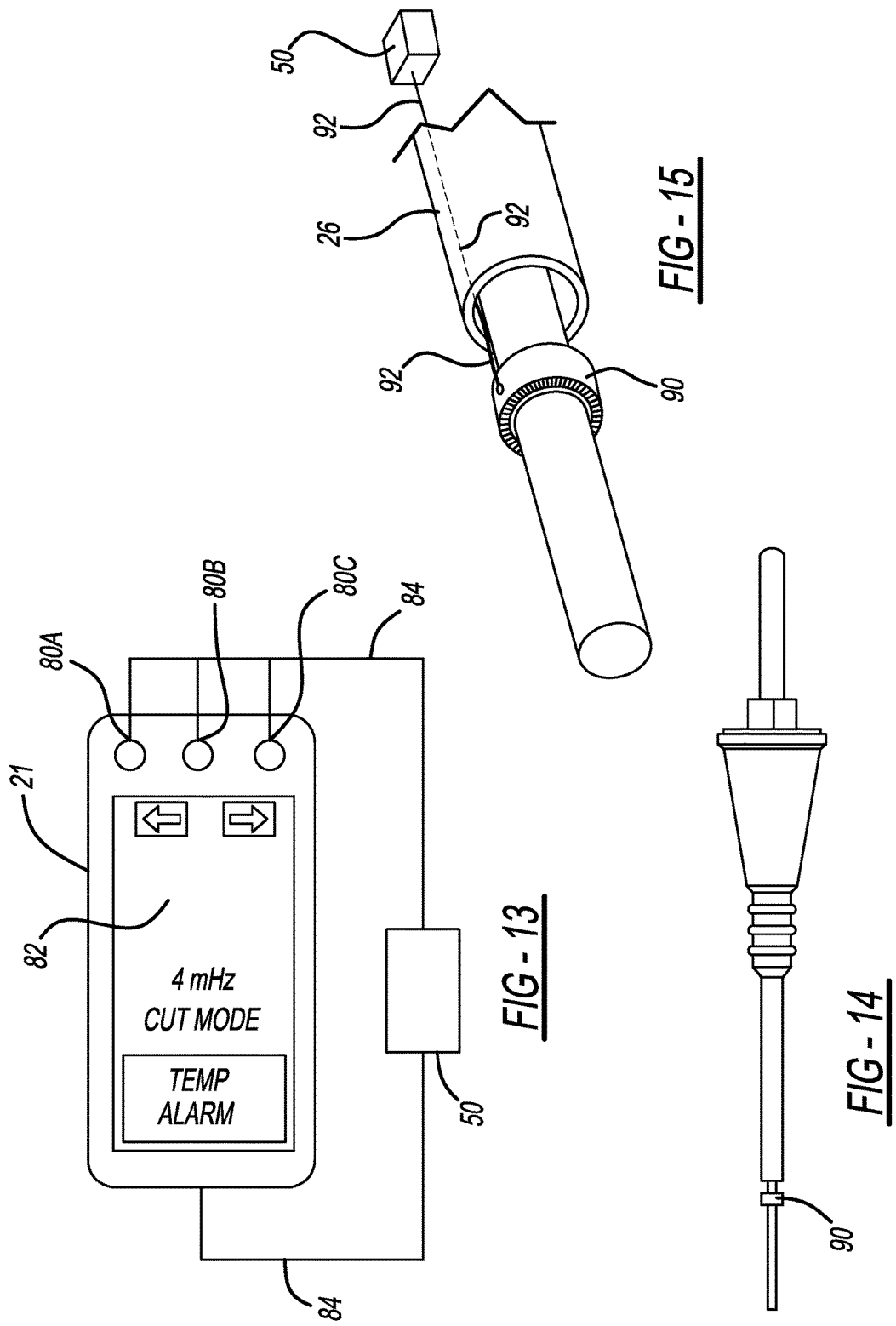

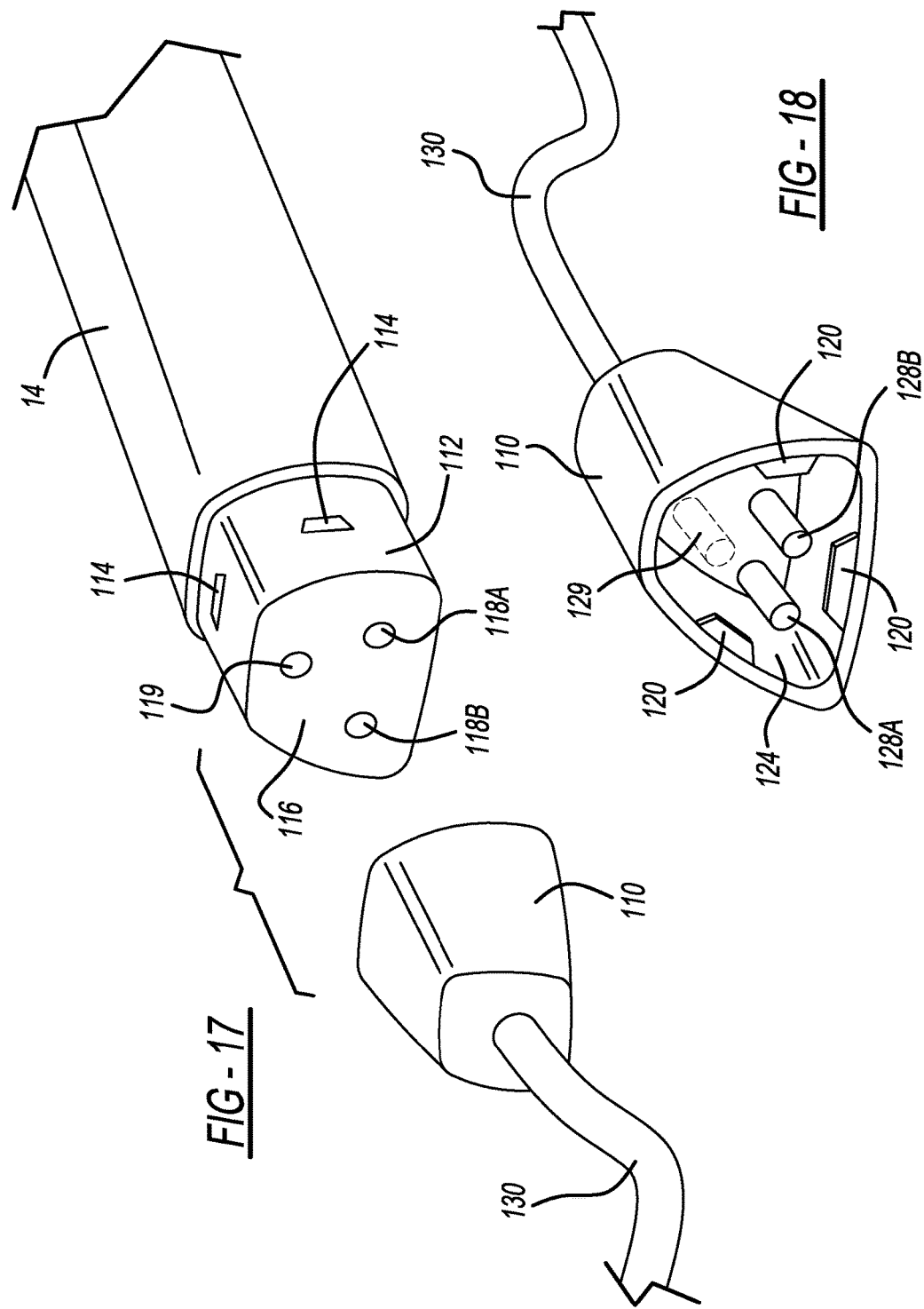

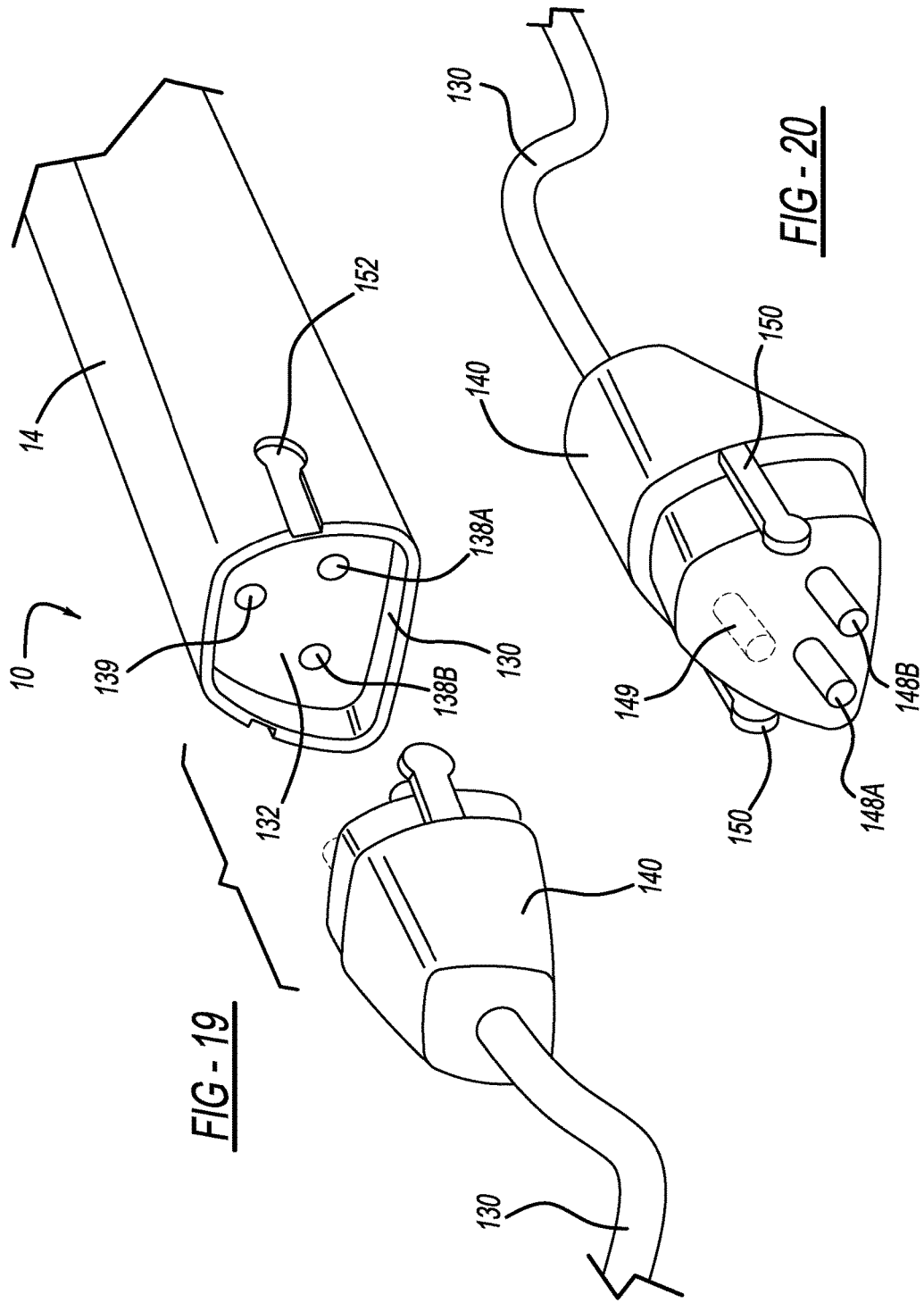

ELECTROSURGICAL HANDPIECE

CROSS REFERENCE TO RELATED APPLICATIONS

The present application claims priority to and is a divisional of U.S. patent application Ser. No. 14/207,990 filed on Mar. 13, 2014, entitled "Electrosurgical Handpiece" to Alan G. Ellman, the entirety of which is hereby incorporated by reference.

BACKGROUND

Electrosurgical instruments are well known and widely used in the medical, dental, and veterinarian fields. In a typical surgical setting, a surgeon may use an electrosurgical instrument to perform a desired cutting procedure and then utilize another electrosurgical instrument to perform a procedure to coagulate blood vessels. Different operational parameters are required for different surgical procedures. It would be desirable to provide an electrosurgical tool configured to provide various settings of the operational parameters with optimum flexibility. An electrosurgical tool which provides a range of operational parameters for surgical procedures such as power settings, temperature control, electrode configurations and RF energy settings would be useful in the surgical field.

SUMMARY OF THE INVENTION

In summary, one embodiment of the present invention is an electrosurgical device for conducting surgical procedures including a handpiece main body, an electrode attachment which is detachable from the handpiece main body, an electrical conduit passing through the main body of the handpiece and a second electrical conduit passing through the electrode attachment so that when the electrode attachment is attached to the handpiece main body, the first and second conduits are electrically connected and power is supplied to the surgical site through the electrode attachment. A feedback unit is positioned within the handpiece main body as well as a feedback path between the feedback unit and the electrode attachment which provides a path for the electrode attachment to send signals to the feedback mechanism. The feedback mechanism responds to the signals through the feedback path to adjust operational characteristics of the device.

BRIEF DESCRIPTION OF THE DRAWINGS

FIG. 1 is a perspective view of a electrosurgical handpiece according to one aspect of the invention;

FIG. 2 is an end view of an electrode attachment for an electrosurgical handpiece according to one aspect of the invention;

FIG. 3 is a perspective view of an electrosurgical handpiece according to an aspect of the invention;

FIG. 4 illustrates handpiece 10 cut along section IV-IV of FIG. 3;

FIG. 5 is a schematic view of an electrical layout for an electrosurgical handpiece according to an aspect of the invention;

FIG. 6 is a cross-section V-V of FIG. 2 of an electrosurgical handpiece according to an aspect of the invention;

FIG. 7 is another embodiment of cross-section V-V of FIG. 2 of an electrosurgical handpiece according to an aspect of the invention;

FIG. 8 is another embodiment of cross-section IV-IV of FIG. 4 of an electrosurgical handpiece according to an aspect of the invention;

FIG. 9 is end view of an electrode attachment for an electrosurgical handpiece according to an aspect of the invention;

FIG. 10 is a perspective view of an electrosurgical handpiece according to an aspect of the invention;

FIG. 11 illustrates an embodiment of an RF unit according to an aspect of the invention;

FIG. 13 illustrates a top view of an embodiment of a visual display according to an aspect of the invention;

FIG. 14 shows an end view of an embodiment of electrode attachment adapted with a vibration mechanism according to an aspect of the invention;

FIG. 15 shows a perspective view of a portion of an electrode attachment adapted with a vibration mechanism;

FIG. 17 shows a perspective view of a detachable electrical connector according to an aspect of the invention;

FIG. 18 shows perspective view of an embodiment of a detachable electrical connector according to an aspect of the invention;

FIG. 19 illustrates a perspective view of an embodiment of a detachable electrical connector according to one aspect of the invention;

FIG. 20 shows a perspective view of an embodiment of a detachable electrical connector according to one aspect of the invention;

DETAILED DESCRIPTION OF PREFERRED EMBODIMENTS

Figure 12:
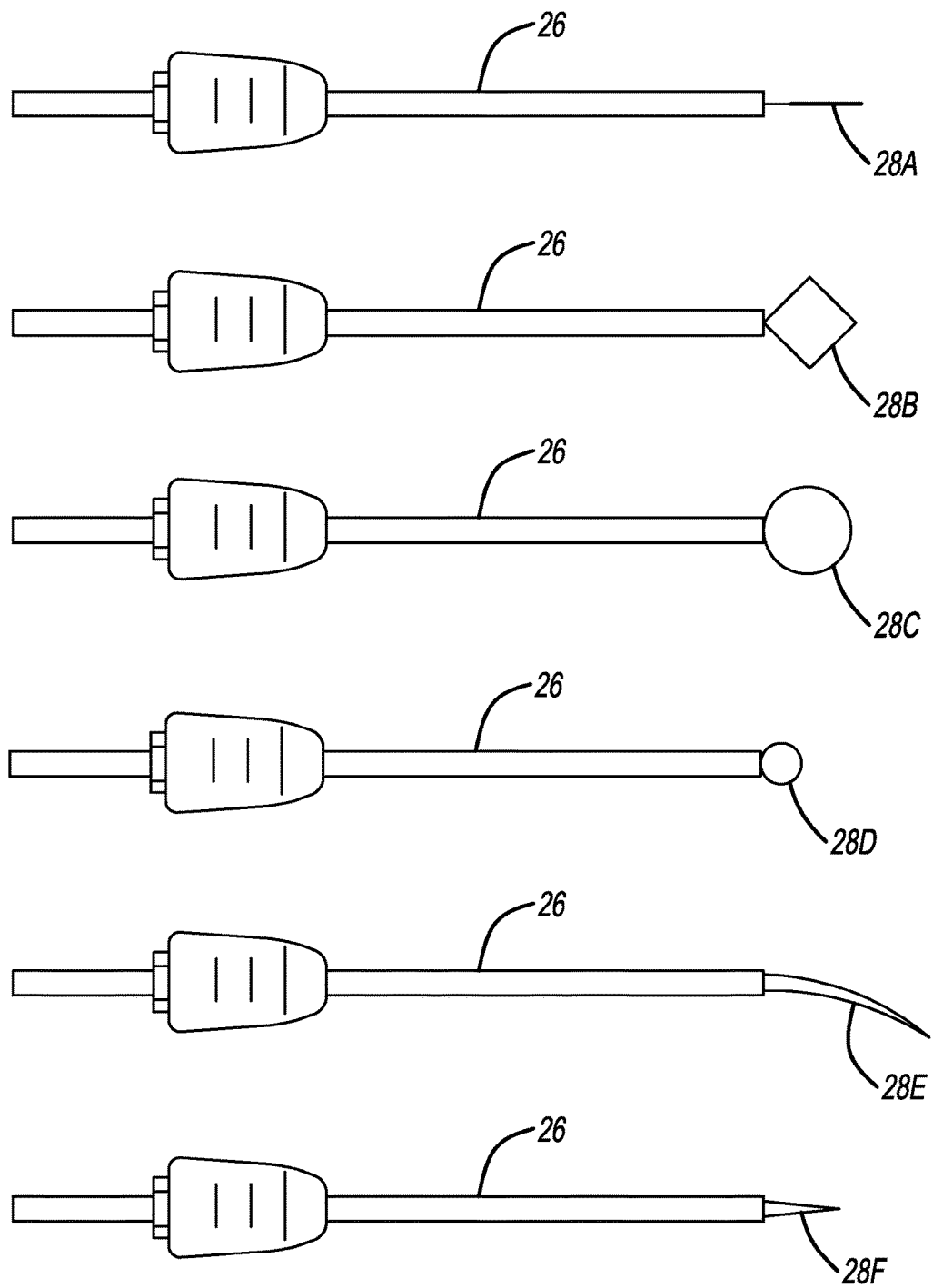
FIG. 12 illustrates embodiments of an electrode attachment according to aspects of the invention.
Figure 16:
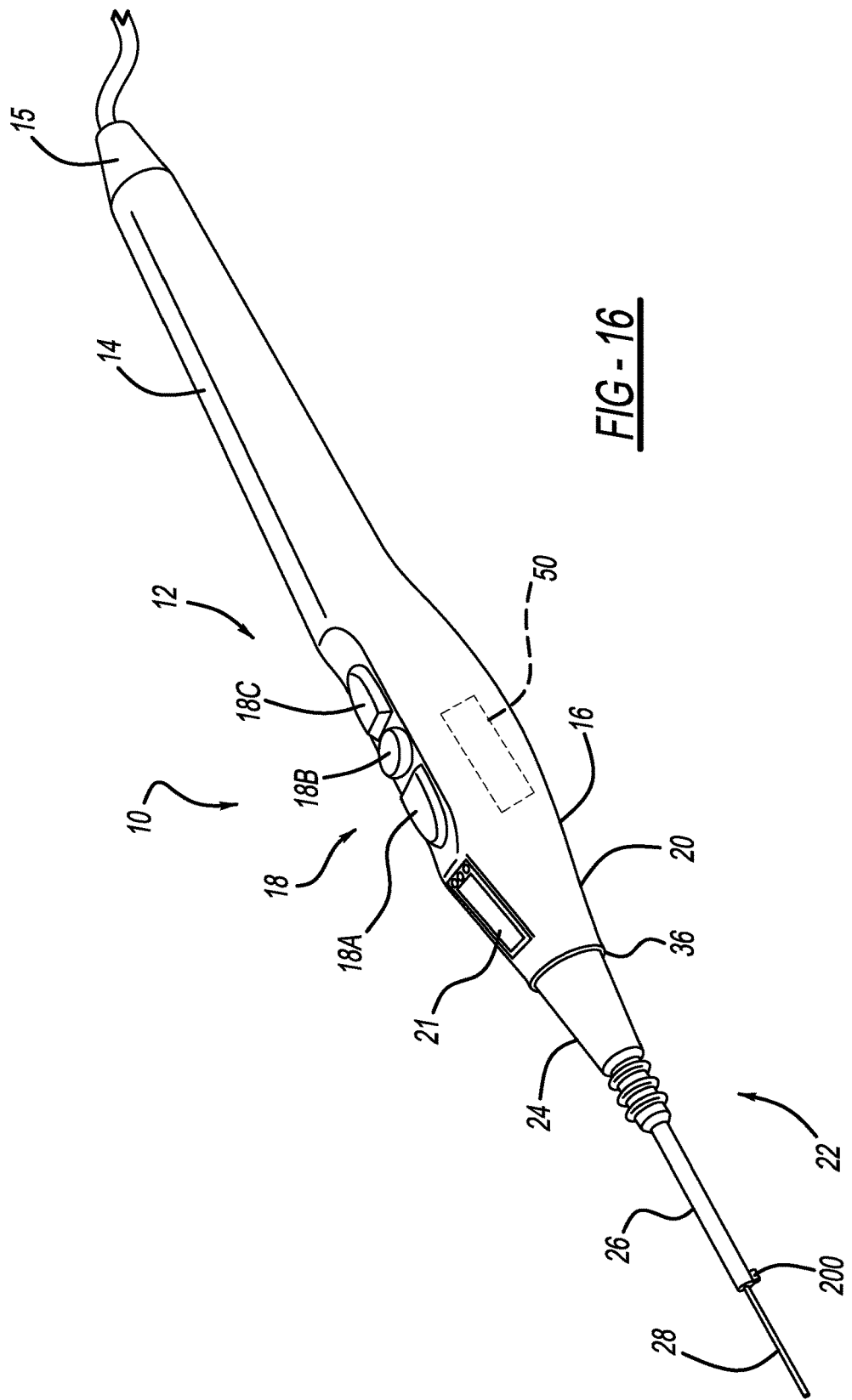
FIG. 16 illustrates a perspective view of an embodiment of an electrosurgical handpiece according to one aspect of the invention.

Referring now to FIG. 1, an electrosurgical device 12 is shown and described. Handpiece 10 generally includes an elongated portion 14 that extends distally away from a grip area 16. In one embodiment, the elongated portion 14 is relatively slim and slender to assist a surgeon as will be described in greater detail hereinafter. U.S. Pat. No. 7,674,261 is incorporated by reference herein.

The grip area 16 is generally thicker and wider than the elongated portion 14 to, in one embodiment, permit the inclusion of electrical components and other components as will be discussed. For example, buttons 18 are provided for operation of the handpiece 10 in accordance with U.S. Pat. No. 7,674,261 the entirety of which is hereby incorporated by reference. More specifically, buttons 18 include "cut" 18A, "hemostasis" 18B, and "combination" 18 C which is a combination of cut and hemostasis. One will recognize that other functionalities may be provided as well in addition to those described herein. The functionality and operation of such buttons 18 are described, in one embodiment, in the aforementioned patent.

Handpiece 10 also includes a tapered region 20 extending from the opposite side of the grip area 16 with respect to the elongated portion 14. Tapered region 20 extends generally from the buttons 18 until reaching the electrode attachment 22. Of course, one skilled in the art will recognize that tapered region 20 may have a different configuration and need not be tapered at all. In one embodiment, the handpiece 10 is a unitary construction of a plastic or other similar type material that provides lightweight and durability to permit a surgeon to conduct surgery in an operative field. The tapered region 20 includes a planar portion beyond the grip area 16 in which a visual display 21, which is described in further detail below, may be located. The visual display 21 provides a visual indication of the status of operational parameters of handpiece 10.

With reference to FIG. 2, electrode attachment 22 is shown in greater detail. In one embodiment, electrode attachment 22 is a detachable and a separate piece from the handpiece 10. Of course, one skilled in the art will recognize that handpiece 10 and electrode attachment 22 may be one unitary construction. In the presently described embodiment, electrode attachment 22 includes a tapered region 24 that extends from the shoulder 36 down to sheath 26. In this fashion when electrode attachment 22 is engaged with handpiece 10 (as will be described), the resulting taper of tapered region 20 and tapered region 24 create a generally uniform and sleek overall taper from the buttons 18 down to the sheath 26. Of course, the effort mentioned unitary taper of tapered region 20 and tapered region 24 need not be uniform and can be an alternate shape or configuration. Sheath 26 extends axially from tapered region 24 in a direction away from the handpiece 10 with respect to when the handpiece 10 is connected with the electrode attachment 22. Sheath 26, in one embodiment, is hollow and cylindrical to permit electrode 28 to pass therethrough. Sheath 26 and tapered region 24 may be constructed of a flexible or rigid material depending on whether or not the surgeon desires to be able to bend or alter the shape or direction of the electrode 28 during a surgical procedure. Electrode 28, similarly, may be constructed of a material that permits bending in accordance with bending of the sheath 26 and tapered region 24. Such materials with respect to the sheath 26 and tapered region 24 may include bendable plastics, elastomers, rubbers, polymers or other suitable materials.

Electrode 28 is constructed of a conductive material and passes through the axial center of both sheath 26 and tapered region 24 to electrically connect with plug 32. Such connection may be through welding or forming the electrode 28 and the plug 32 is one unitary piece surrounded by sheath 26 and tapered region 24. One skilled in the art will readily recognize alternative manufacturing methods that may be employed.

Plug 32 is structurally supported by and positioned within tapered region 24. Positioned around plug 32 and engaged with shoulder 36 is a key 34. Key 34, in one embodiment, is hexagonally shaped for reasons that will become more clear with the following description. Furthermore, it will be noted that key 34 may be any alternate shape such as a square, triangle, rectangle or other shape that locks electrode attachment 22 rotationally in place with respect to handpiece 10 as will be described. In the present embodiment, electrode attachment 22 remains fixed rotationally with respect to handpiece 10 during use by a surgeon through a meeting of the hexagonal shape of key 34 with the handpiece 10 as will be described.

Referring to FIG. 3, FIG. 4 and FIG. 2, the attachment of handpiece 10 with electrode attachment 22 is shown and described. With reference to FIG. 3, handpiece 10 is shown with electrode attachment 22 removed. In this configuration, handpiece 10 includes plug receptacle 38 and key receptacle 40. Referring to FIG. 2, it will be understood and appreciated that plug receptacle 38 is a cylindrical hollow receptacle that receives plug 32 in an electrically connected fashion. For example, plug receptacle 38 may create an interference fit with plug 32 such that the outer wall of plug 32 is pressed against the inner wall of plug receptacle 38. Referring to FIG. 4, key receptacle 40 includes walls 42 that are also hexagonally positioned such that the inside of the hexagonally walls 42 abut against the hexagonally outer region of key 34. The result is that key receptacle 40 and key 34 interact to prevent rotation of electrode attachment 22 with respect to handpiece 10.

With reference to FIG. 5 and FIG. 6, another embodiment of the present invention is shown and described. In the presently described embodiment, the rotational position of the electrode attachment 22 will result in the handpiece 10 in providing different voltage, waveform or other electrical characteristics to electrode 28. For example, if the electrode attachment 22 is in one angular position with respect to the handpiece 10 such that certain portions of key 34 mate with certain portions of walls 42, then a specific electrical signal will be provided to the electrode 28 by the handpiece 10. Likewise, if a surgeon were to rotate the electrode attachment 22 a certain angular displacement (for example 180°) from this initial position, then a different electrical signal will be provided to electrode 28.

With reference to FIG. 5, one embodiment for accomplishing the electrical response is shown and described. FIG. 5 is an electrical schematic according to one aspect of the present invention. The electrical schematic shown in FIG. 5 may occur within handpiece 10, in accordance with the present embodiment. Alternatively, the electrical schematic described herein may be performed in an attached RF unit or feedback unit.

FIG. 5 illustrates handpiece 10 cut along section IV-IV of FIG. 3 similar to that shown in FIG. 4. However, in the presently described embodiment, walls 42 include electrical contacts 44 positioned on at least one or possibly all of the walls 42. The electrical contacts 44 pass through the walls 42 such that the outer walls of key 34 or electrode positioned thereon will create an electrical connection with electrical contacts 44. Each of the contacts 44 is connected to a respective electrical connection 46 (for example a wire) that connects back to feedback unit 50. The electrical connection 46 may pass through the handpiece 10 or alternatively around or through separate wires from the handpiece 10. The feedback unit 50 may be any suitable device such as an IC chip, logic controller or computer that is programmed or configured to output a response to RF unit 51 (for example through an electrical signal) based on conditions of the electrical signal provided along electrical connection 46. Between the contacts 44 and the feedback unit 50 are, in one embodiment, circuitry 48. Circuitry 48 could be, in one example, a resistor, transistor, capacitor, inductor or other circuit device that alters the characteristics of an electrical signal passed from feedback unit 50 to contacts 44.

Feedback unit 50 is operatively connected to RF unit 51 to control characteristics of the RF unit 51 based on certain conditions as will be described. RF unit 51 provides an electrical power source at given frequencies, voltages and amperages as described in the aforementioned patent incorporated herein by reference. The electrical power is generated by the RF unit 51 and is transmitted through power connection 52 to plug receptacle 38. Plug receptacle 38, given its electrical connection to plug 32, transmits the power to plug 32 and therefore to electrode 28. The result is electrical power provided to the electrode 28 such that the surgeon can perform the electrical procedures as described in the aforementioned patent.

With reference to FIG. 6, a similar cross-section V-V as shown in FIG. 2 is provided. However, in the embodiment shown in FIG. 6, contact 54 is positioned on one of the outer walls of key 34. The contact 54, in one embodiment, is grounded through ground 56. It will be understood however that multiple contacts 54 may be positioned on multiple outer walls of key 34 to elicit different electrical responses.

With continued reference to the figures, the operation of the presently described embodiment will now be described. In operation, feedback unit 50 provides a common electrical signal across each of the electrical connections 46. The electrical signal passes through each one of the respective circuitry 48 and to the contacts 44. When electrode attachment 22 is engaged with handpiece 10, the contact 54 shown in FIG. 6 will connect with one of the contacts 44 shown in FIG. 5. Accordingly, only one of the electrical connections 46 will result in a complete circuit. As such, feedback unit 50 detects which of the electrical connections 46 results in a complete circuit and therefore can respond by instructing RF unit 51 to elicit a specific electrical signal to electrode 28 depending on which one of the electrical connections 46 results in a complete circuit. Practically speaking, therefore, if a surgeon were to rotate electrical attachment 22 angularly, thereby causing different connections between one of the contacts 44 and contact 54, the result would be different electrical connections 46 being energized dependent upon the angular position of electrode attachment 22, thereby resulting in different electrical signals to electrode 28.

Alternatively, in another embodiment, multiple contacts 54 may be provided on key 34. As such, simply measuring which of the electrical connections 46 are grounded may not be sufficient. Therefore, circuitry 48 may be used to distinguish one of the electrical connections 46 from others. Circuitry 48 may include different characteristics for each one of the electrical connections 46 (for example different resistors) and therefore result in a different voltage/current relationship for each of the electrical connections 46. As such, feedback unit 50, detecting different voltage/current relationships on each of the electrical connections 46, will be able to determine which of the electrical contacts 4 are energized.

In another embodiment, contact 54 connects to plug 32 instead of a ground. In this embodiment, feedback unit 50 reads characteristics of the electrical power provided to the electrode 28 from the contact 54 connected to the plug 32 when the handpiece 10 is being used. Here, RF unit 51, during operation, can instruct the RF unit 51 to alter the signal provided to electrode 28 based on such characteristics. For example, feedback unit 50 may determine the amount of time for which power is supplied to the electrode 28 and therefore how long the handpiece 10 is in use and, based upon such time, stop the unit from being able to be further operated. The result would be a timer that permits a surgeon to use the handpiece only for a specific amount of time. Similarly, feedback unit 50 may determine whether too much power is being provided to the electrode or whether the electrode is overheating and may instruct the RF unit 51 to alter its power output to the electrode.

With respect to FIG. 7 in FIG. 8, another embodiment of the present invention shown and described. FIG. 7 shows another cross-section V-V along FIG. 2 and FIG. 8 shows another cross-section IV-IV along FIG. 4. In the presently described embodiment, an additional key 58 is provided to key 34. In a similar fashion, a key receptacle 61 is provided from key receptacle 40. Although the present key and key receptacle combination is illustrated as a slot and receiver configuration, it will be understood by one skilled in the art that other suitable key and key receptacle configurations may be used other than that described herein.

In the presently described embodiment, electrode attachment 22 is rotated angularly with respect to handpiece 10 until key 58 aligns with key receptacle 61. When this alignment is made, then electrode attachment 22 may be axially positioned into handpiece 10 through the key and key receptacle arrangement described herein. With reference to the previously described embodiments, the result would be a specific location of contact 54 with a specific one of contacts 44. Feedback unit 50 will then receive a signal of a completed electrical connection 46 and any outputs from circuitry 48. In response, feedback unit 50 sends feedback signal to RF unit 51 to adjust operational settings for electrode attachment 22 and feedback unit 50 may send feedback signals to other components of the handpiece 10 for adjustment of operational parameters.

In operation, a multitude of different electrode attachments 22 may be provided to a surgeon with different key configurations. The different key configurations would result in contact 54 aligning with specific one of contacts 44, thereby eliciting a specific one of the electrical connections 46 being energized and therefore resulting in feedback unit 50 instructing RF unit 51 to initiate different electrical power to electrode 28 depending on which one of the electrode attachments 22 that are used. As such, a multitude of different electrode attachments 22 may be provided to a surgeon such that the surgeon need only connect a specific electrode for a specific procedure into the handpiece 10.

The key relationship will ensure that the correct electrode attachment 22 is used for a specific procedure. For example, a blue colored electrode attachment 22 may be used for hemostasis. Therefore, the blue colored electrode attachment 22 is keyed in such a configuration that would result in the feedback unit 50 mandating that the RF unit 51 output a specific power setting required for hemostasis. One will understand that different colors or different markings on different electrode attachments 22 may be used to generate a different power output from the RF unit 51.

It will be noted that electrical connection between plug 32 and plug receptacle 38 as well as between handpiece 10 and RF unit 51 may be, instead of a direct electrical connection, Bluetooth, inductive connected or other wireless type of connections. Similarly, the connections between contacts 44 and contact 54 may likewise be a wireless connection such as Bluetooth, inductive or other means.

With reference to FIG. 9 and FIG. 10, another embodiment of the present invention is shown and described. In FIG. 9, electrode attachment 22 includes an additional passage 62 that passes from shoulder 36 down to sheath 26. As sheath 26 is hollow and spacing exist between electrode 28 and the inner wall of sheath 26, a passage is made from shoulder 36 to mist opening 64. A similar passage mating against passage 62 at shoulder 36 passes through handpiece 10. A hose 66 connects from an exit area on handpiece 10 and connects to RF unit 61 or, alternatively, a separate mist generating unit.

Referring to FIG. 11, RF unit 61 is shown with a hose 66 passing therethrough and connecting to a bag 70 or other holding device through bag connection 72. Although a bag is shown, it will be understood that any mechanism or container holding the required material may be provided.

In operation, RF unit 61 draws a medium from bag 70 and provides it in a mist form through hose 66 through a known means of generating mist. The medium provided from bag 70 may be any of a multitude of mediums such as hot or cold steam, hot or cold air, medication, pain relievers, anticoagulants, antibiotics, moisturizers, or any other suitable mediums that may be used in a surgical environment. The steam is provided from RF unit 61, transmitted through the apertures in handpiece 10, through the passage 62 and mist opening 64 and thereby enters the operative area of the patient. It will also be understood that an alternative means of providing such mist may be used such as, including but not limited to, a tube attached to the outside of the handpiece 10, a secondary tube provided alongside sheath 26 and passing through the handpiece 10 or alternate suitable means. Likewise, generation of such steam may be in the form of the use of liquid nitrogen, heating, diffuser, vaporization or other suitable means of generating mist.

In an alternative embodiment, instead of the use of three different buttons 18 A, 18 B and 18C, one button may be provided or, alternatively, a foot switch may be used. Such an embodiment may be conducive with the characteristics described with respect to the embodiments of FIG. 5 and FIG. 6 such that a particular electrode attachment 22 may be only conducive and connect with the handpiece 10 to generate a cut mode. Likewise, another electrode attachment 22 may be configured in such a way that only a hemo-mode may be used. As such, a particular electrode attachment 22 may be keyed such that the feedback unit 50 initiates a specific electrical signal only designed for that specific electrode attachment 22. In this way, the surgeon's requirement to know which button to push is minimized. In another embodiment, the electrode attachments 22 may be color coded, marked or alternatively distinguishable such that a surgeon will know that a specific electrode attachment 22 is for use with specific surgical procedures such as cutting or hemo.

With reference to FIG. 12, other embodiments of the electrode 28 are shown and described. For example, electrode 28A is shown as a wire extending from sheath 20. Electrode 28B is shown as either a solid diamond shape or a wire shaped as a diamond extending from sheath 20. Electrode 28C is shown as a relatively large sphere or circular shaped wire extending from sheath 20. Electrode 28D is shown as a relatively smaller sphere or circular wire extending from sheath 20. Electrode 28E is shown as an angled or curved wire extending from sheath 20. Electrode 28F is shown as a pointed electrode extending from sheath 20.

FIG. 13, a schematic view of visual display 21, includes light features 80A, 80B, and 80C located adjacent to display screen 82 and in electrical communication with feedback unit 50. Light features 80A, 80B and 80C may be colored LED's or other light indicators used to provide visual status of various operational parameters of the electrosurgical tool. Although the LED's 80A, 80B, 80C are illustrated as being positioned along one edge of the visual display 21, one skilled in the art will recognize that the LEDs 18 may be positioned at any convenient location on the informational display 21 or elsewhere on the handpiece 10. LED 80A, 80B, 80C may be lit to indicate power on or off or they may be color-coded for more detailed information. For example a green LED 80A may be lit to indicate that the "cut" feature has been selected while a blue LED 80B may be lit indicate that the "hemostatis" feature is in operation. Both the blue and green LEDs may be lit to indicate the "combo" feature. A red LED 80C may light to indicate an alarm status such as a temperature alarm. The indicator LED's 80 can be used to provide a visual status of other handpiece 10 and electrode attachment 22 functions such as whether the electrode is in a bipolar or monopolar power mode, frequency settings or any system alarm.

FIG. 13 illustrates visual display 21 including display screen 82 which may be an LCD or other display technology. Display screen 82 provides a status of handpiece 10 operations such as temperature settings and alarms, bipolar or monopolar power settings, time of operation, and any other desirable information for the operation of the electrosurgical device 12. In one embodiment, visual display includes stationary or flashing text string as part of a visual indicator. Display screen 82 may include a touch screen type of user interface wherein the user of the handpiece 10 may touch a portion of the screen to change the information displayed or to select a particular operation or feature of the handpiece 10.

In continuing reference to FIG. 13, display screen 82 receives signals from the feedback unit 50 along electrical connectors 84 to receive information about the operational status of the handpiece 10 for display on the display screen 82. Information and settings may be continuously sent between feedback unit 50 to the display screen 82 for updated displays. If the feedback unit 50 determines that a functional aspect of the handpiece 10 is out of compliance, such as temperature, it can send a signal to either or both LEDs 80A, 80B, 80C and display screen 82 to provide a visual message. LED 80A, 80B or 80C may be lit or a flashing text message may appear on the display screen 82. Display screen 82 and LEDs 80A, 80B, and 80C of the handpiece 10, in one embodiment, are resistant to moisture and compatible with the requirements of electronic components in a surgical tool.

FIGS. 14 and 15 illustrate a vibrating mechanism 90 positioned in engagement with the electrode 28 to permit the vibrating mechanism 90 to induce vibration into the electrode 28 as will be described. In one aspect, the vibrating mechanism 90 is mechanically isolated from the rest of the hand piece so as not to induce vibration in the user's hand. This can be achieve through a number of means of vibrational isolation including, but not limited to, rubber or elastic mounts between the electrode and the handpiece 10. Alternately the vibrational movement of the electrode is so small as to not interfere with the ability of the surgeon to accurately position the handpiece 10 and its incorporated electrode 28 to the desired location in the operative field. The vibrating mechanism 90 may be in the form of a miniature actuator such as a piezo ceramic actuator attached to the electrode 28 which creates a vibration movement in the electrode 28 when activated. Other devices that are known in the art may be employed to create the vibrations. The vibrating mechanism 90 may be electrically connected by an electrical connection 92 to the feedback unit 50 as shown in FIG. 15. Vibrating mechanism 80 may be used to enhance the performance of electrode 28 for surgical operations such as cutting. For example, when electrode 28 is energized, vibrating mechanism 90 may operate at initial settings for frequency, amplitude, wavelength, duration or other operational settings of vibrating mechanism 90, which may change as the surgical procedure progresses. In another embodiment, for a particular mode of surgery or other input to the handpiece 10, a signal may be sent from feedback unit 50 to vibrating mechanism 90 to operate with predetermined settings or changing settings. In yet another embodiment, sensor 200 may provide sensing input from electrode 28 or other inputs from the surgical site adjacent electrode 28 to feedback unit 50, which, in turn, may adjustment the operational settings of vibrating mechanism 90. If feedback unit 50, through measurement of various system attributes such as power levels over time or input from sensor 200, determines that the electrode 28 is delayed in energizing, a signal may be sent to the vibrating mechanism 90 to initiate a mechanical vibration effect which, in turn, causes the electrode 28 to vibrate at a frequency for energizing the electrode 28. Sensor 200 may be located on the outside of the sheath for detection of operational parameters related to the control of the vibration mechanism 90. Further description of the sensor 200 is provided below.

FIGS. 17 and 18 illustrate an embodiment of a power connector 15 which is configured at the end of the slender portion 14 of the handpiece 10. Power connector 15 provides the option to connect either a bipolar or monopolar electrical connection to the handpiece so that either a bipolar or monopolar electrode 28 may be used with the handpiece 10. In this embodiment, the slender portion 14 of the handpiece 10 narrows downward into a necked region 112 which fits snugly into the recessed portion 124 of a power plug 110 which in turn connects to a power source through electrical cord 130. Beyond the necked region 112, the slender portion 14 ends in a planar surface 116. The planar surface 116 includes one or more receptacles 118A, 118B, 119 into which an electrical connection can be made. The necked portion 112 may include openings 114 into which a clip or spring feature 120 on the interior of the power plug 110 can be inserted for a secure coupling of the handpiece 10 to the power plug 110. FIG. 18 illustrates the interior view of the power plug 110 which includes prongs 128A, 128B, and 129. In one embodiment of this invention, prongs 128A and 128B are inserted into receptacles 118A and 118B for bipolar mode operation. In another embodiment, prong 129 is inserted into receptacle 119 for monopolar mode operation.

An alternate embodiment of the power connector 15 is shown in FIGS. 19 and 20 in which the slender end 14 of the handpiece 10 terminates in a recessed region 130 and includes a planar surface 132 at the back of the recessed region 130 for positioning of receptacles 138A and 138B an2d 139. In this embodiment, the power plug 140 has a necked portion 142 for positioning prongs 148A and 148B and 149 for electrical connection to the receptacles 138A, 138B, 139 in the recessed portion of the handpiece 10. In an embodiment of invention, prongs 148A and 148B may be adapted for bipolar connection to receptacles 138A and 138B, while prong 1439 may be adapted for monpolar connection to receptacle 139. Those skilled in the art will recognize that many different configurations of electrical prong connectors may be configured to connect with different configurations of receptacles to provide different power modes of handpiece 10 operation. In one embodiment, power adapter 15 is made of lightweight materials such as plastic or ceramic which will not interfere with the sleek and balance design of the handpiece 10 for its use as a surgical instrument.

Figure 21:
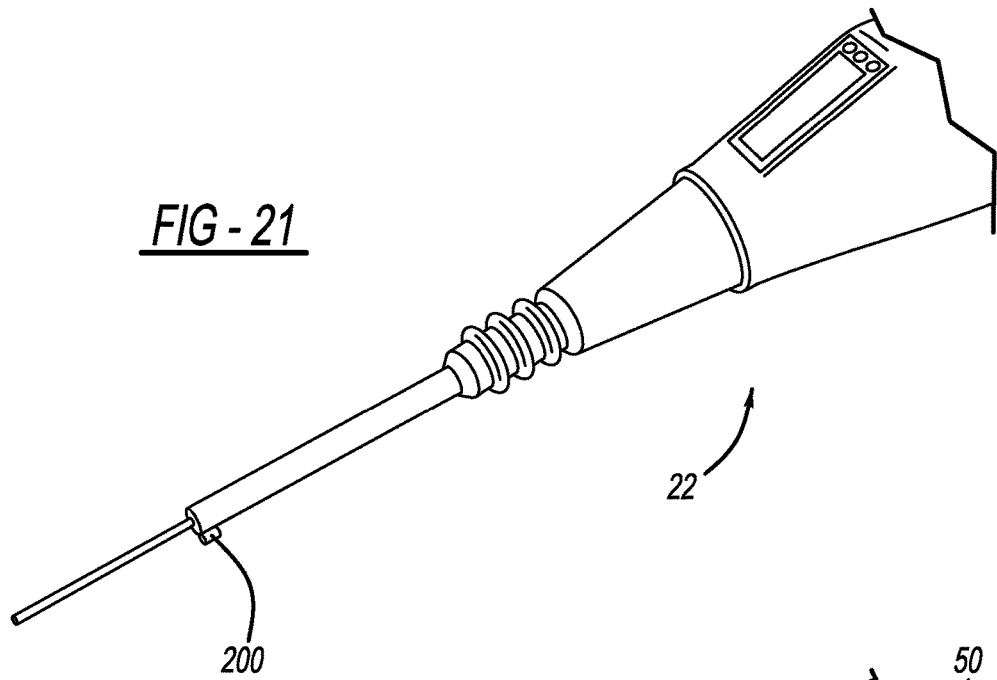
FIG. 21 shows a perspective view of an embodiment of an electrode attachment adapted with a sensor according to an aspect of the invention.
Figure 22:
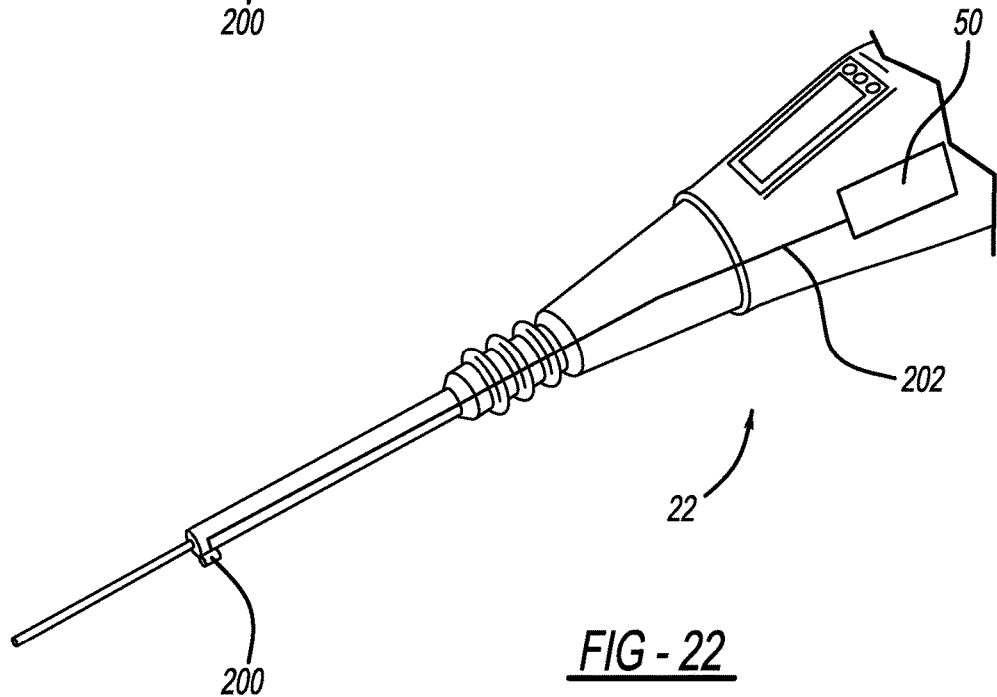
FIG. 22 shows perspective view of an embodiment of and electrode attachment adapted with a sensor according to an aspect of the invention.

Referring now to FIG. 21, another embodiment of the invention is shown and described. In FIG. 20, handpiece 10 is shown having a sensor 200 positioned at a distal end of an electrode 28 with respect to the grip area 16. A wire, optical cable or other connection 202 connects the sensor 200 with the feedback unit 50. In one embodiment, the sensor 200 is a thermal sensor that senses the temperature of the tip of the electrode 28 or, alternatively, the temperature of the operative area in which the device is being used. In another embodiment, the sensor 200 is a vibrational sensor that senses the vibration, amplitude, frequency, wavelength, or other periodic oscillatory movements of the electrode 28. If a vibrational sensor 200 is employed, it will be understood that the vibrational sensor 200 may be located at different points along the electrode 28. For example, the vibrational sensor 200 may be incorporated into vibrating mechanism 90 or instead engaged with the electrode itself.

Feedback unit 50 receive signals indicative of these measurements and in response thereto adjusts the movement of the electrode 28 through use of the vibrating mechanism 90 as described previously. Or in another embodiment, feedback unit 50 varies the electrical signal in response to the conditions measured by the sensor 200. For example, if the temperature measured by sensor 200 is too high, feedback unit 50 may reduce the amount of current flow. Alternatively, feedback unit 50 may alter the frequency, wavelength, amplitude or other features depending on the conditions in the operative area.

In this specification, various preferred embodiments may have been described with reference to the accompanying drawings. It will, however, be evident that various modifications and changes may be made thereto, and additional embodiments may be implemented, without departing from the broader scope of the invention as set forth in the claims that follow. The present invention is thus not to be interpreted as being limited to particular embodiments and the specification and drawings are to be regarded in an illustrative rather than restrictive sense.

It will be appreciated that the system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A device for conducting surgical procedures, comprising:
   a handpiece main body;
   an electrical conduit passing through the handpiece main body;
   an electrode attachment detachably connected to the handpiece main body;
   a second electrical conduit passing through the electrode attachment that electrically connects to the electrical conduit when the electrode attachment is attached to the handpiece main body, wherein the electrical conduit and second electrical conduit provide an electrical path for passing electrical current to a surgical operative field;
   a feedback mechanism positioned within the handpiece main body;
   a feedback electrical path between the electrode attachment and the feedback mechanism; and
   a key interface connecting the electrode attachment and the handpiece main body, wherein the key interface further comprises a first electrical contact on the handpiece main body and a plurality of second electrical contacts on the electrode attachment;
   wherein the key interface aligns the first electrical contact and one of the second electrical contacts to transmit an electrical signal to the feedback mechanism to adjust operational parameters of the device;
   the key interface further comprises a plurality of keyed positions, each of said keyed positions corresponding to one of the second electrical contacts;
   each one of said second electrical contacts providing a different signal to the feedback mechanism when connected to the first electrical contact to result in a different adjustment of the operational parameters of the device depending on which of the plurality of second electrical contacts is connected to the first electrical contact; and
   the electrode attachment is adapted for rotatable insertion into the handpiece main body to permit selective engagement between the first electrical contact and each one of the second electrical contacts associated with the keyed positions.

2. The device according to claim 1, wherein the selection of one of the plurality of keyed positions aligns the first contact with one of the plurality of second contacts on a key structure to transmit the electrical signal to the feedback mechanism to adjust the operational parameters of the device.

3. The device according to claim 2, wherein the selection of the keyed position of connection determines a mode of surgical operation of the device.

4. A device according to claim 3, further comprising:
   at least a first electrical circuit in electrical communication between the first electrical contact and the feedback mechanism;
   wherein the first electrical circuit modifies the electrical signal between the first
   electrical contact and the feedback mechanism.

5. A device for conducting surgical procedures, comprising:
   a handpiece main body;
   an electrical conduit passing through the handpiece main body;
   an electrode attachment detachably connected to the handpiece main body;
   a second electrical conduit passing through the electrode attachment that electrically connects to the electrical conduit when the electrode attachment is attached to the handpiece main body, wherein the electrical conduit and second electrical conduit provide an electrical path for passing electrical current to a surgical operative field;
   a feedback mechanism positioned within the handpiece main body;
   a feedback electrical path between the electrode attachment and the feedback mechanism; and
   a key interface connecting the electrode attachment and the handpiece main body, wherein the key interface further comprises at least one first electrical contact on the handpiece main body and at least one second electrical contact on the electrode attachment;
   wherein the key interface aligns the at least one first electrical contact and the at least one second electrical contact to transmit an electrical signal to the feedback mechanism to adjust operational parameters of the device;
   wherein the key interface further comprises a plurality of keyed positions, each of said keyed positions corresponding to a respective second electrical contact of the at least one second electrical contact;
   wherein each second electrical contact provides a different signal to the feedback mechanism when connected to the at least one first electrical contact to result in a different adjustment of the operational parameters of the device depending on which second electrical contact is connected to the at least one first electrical contact; and
   wherein the electrode attachment is adapted for rotatable insertion into the handpiece main body to permit selective engagement between the at least one first electrical contact and a selected one of the second electrical contacts.

* * * * *